US011793656B2

(12) United States Patent
Henkes et al.

(10) Patent No.: US 11,793,656 B2
(45) Date of Patent: Oct. 24, 2023

(54) IMPLANT INSERTION SYSTEM

(71) Applicant: Phenox GmbH, Bochum (DE)

(72) Inventors: Hans Henkes, Stuttgart (DE);
Hermann Monstadt, Bochum (DE);
Ralf Hannes, Dortmund (DE); Stefan Rolla, Bochum (DE); Manuel Salin, Bochum (DE)

(73) Assignee: phenox GmbH, Bochum (DE)

( * ) Notice: Subject to any disclaimer, the term of this patent is extended or adjusted under 35 U.S.C. 154(b) by 0 days.

(21) Appl. No.: 17/518,974

(22) Filed: Nov. 4, 2021

(65) Prior Publication Data
US 2022/0110763 A1   Apr. 14, 2022

Related U.S. Application Data

(63) Continuation of application No. 15/555,738, filed as application No. PCT/EP2016/054692 on Mar. 4, 2016, now Pat. No. 11,166,827.

(30) Foreign Application Priority Data

Mar. 5, 2015   (DE) .......................... 102015103240.6

(51) Int. Cl.
*A61F 2/46*   (2006.01)
*A61F 2/966*   (2013.01)
(Continued)

(52) U.S. Cl.
CPC ............ *A61F 2/4603* (2013.01); *A61F 2/243* (2013.01); *A61F 2/966* (2013.01); *A61F 2/0027* (2013.01);
(Continued)

(58) Field of Classification Search
CPC .......... A61F 2/243; A61F 2/966; A61F 2/958; A61F 2/90; A61F 2/0027; A61F 2/91;
(Continued)

(56) References Cited

U.S. PATENT DOCUMENTS

| 5,026,377 A | 6/1991 | Burton et al. |
| 6,875,197 B1 | 4/2005 | Simhambhatla et al. |
| (Continued) | | |

FOREIGN PATENT DOCUMENTS

| EP | 2628470 | 8/2013 |
| JP | 357465 | 3/1991 |
| (Continued) | | |

OTHER PUBLICATIONS

Notice of Grounds for Rejection dated Oct. 2, 2019 from Japanese Patent Application No. 2017-546683.
(Continued)

*Primary Examiner* — Marcela I. Shirsat
(74) *Attorney, Agent, or Firm* — Crockett & Crockett, PC; K. David Crockett, Esq.

(57) ABSTRACT

A device for introducing an implant (1) into blood vessels or hollow organs of the human or animal body. The device includes an implant (1), an insertion wire (14) and a release tube (13), wherein the implant (1) is deformable so that it fits into a microcatheter (8) and expands once the external constraint of the microcatheter (8) disappears, adapting to the diameter of the blood vessel or hollow organ, wherein a holding element (2) is arranged on the insertion wire (14) and the holding element (2) has at its periphery at least one groove (3) set into the holding element (2), running along the circumference of the holding element (2) and forming tracks in the form of curved lines, wherein the implant (1) has holding wired (5) extending proximally, which are fitted into the grooves (3).

16 Claims, 6 Drawing Sheets

(51) Int. Cl.
- *A61F 2/82* (2013.01)
- *A61F 2/90* (2013.01)
- *A61F 2/07* (2013.01)
- *A61F 2/844* (2013.01)
- *A61F 2/86* (2013.01)
- *A61F 2/95* (2013.01)
- *A61F 2/00* (2006.01)
- *A61F 2/24* (2006.01)
- *A61F 2/01* (2006.01)

(52) U.S. Cl.
CPC .............. *A61F 2/011* (2020.05); *A61F 2/07* (2013.01); *A61F 2/844* (2013.01); *A61F 2/86* (2013.01); *A61F 2/90* (2013.01); *A61F 2/95* (2013.01); *A61F 2/9522* (2020.05); *A61F 2002/823* (2013.01); *A61F 2002/9505* (2013.01); *A61F 2002/9665* (2013.01)

(58) Field of Classification Search
CPC ........ A61F 2/4603; A61F 2/013; A61F 2/844; A61F 2002/823; A61F 2002/9665; A61F 2002/011; A61F 2/011; A61F 2/07; A61F 2/82; A61F 2/86; A61F 2/95; A61F 2/9522; A61F 2002/9505; A61F 2002/9583; A61M 2025/0042; A61B 5/6862
USPC ..... 606/99; 623/1.11, 1.12, 1.18, 1.23, 1.15, 623/900, 1.2, 23.7
See application file for complete search history.

(56) References Cited

U.S. PATENT DOCUMENTS

| | | |
|---|---|---|
| 9,867,726 B2 | 1/2018 | Aporta et al. |
| 2005/0049670 A1 | 3/2005 | Jones et al. |
| 2006/0155357 A1* | 7/2006 | Melsheimer .............. A61F 2/95 623/1.11 |
| 2009/0264978 A1 | 10/2009 | Dieck et al. |
| 2010/0152834 A1* | 6/2010 | Hannes ..................... A61F 2/90 623/1.46 |
| 2011/0218613 A1 | 9/2011 | Leopold et al. |
| 2012/0078350 A1 | 3/2012 | Wang et al. |
| 2012/0143237 A1 | 6/2012 | Cam et al. |
| 2012/0226343 A1 | 9/2012 | Vo et al. |
| 2013/0123901 A1 | 5/2013 | Connor et al. |
| 2013/0218138 A1 | 8/2013 | Fargahi |
| 2013/0226278 A1 | 8/2013 | Newell et al. |
| 2014/0277361 A1 | 9/2014 | Farhat et al. |

FOREIGN PATENT DOCUMENTS

| | | |
|---|---|---|
| JP | 2005125102 | 5/2005 |
| JP | 2013500792 | 1/2013 |
| JP | 2013248332 | 12/2013 |
| WO | WO2011014814 | 2/2011 |
| WO | WO2011147567 | 12/2011 |
| WO | WO2012009006 | 1/2012 |
| WO | WO2013138519 | 9/2013 |

OTHER PUBLICATIONS

Examination Report dated Feb. 28, 2020 from Indian Patent Application No. 201747034325.
Notice of Reasons for Refusal dated May 25, 2021 from Japanese Patent Application No. 2017-546683.
International Search Report dated Jan. 6, 2016 from International Application PCT/EP2016/054692.

* cited by examiner

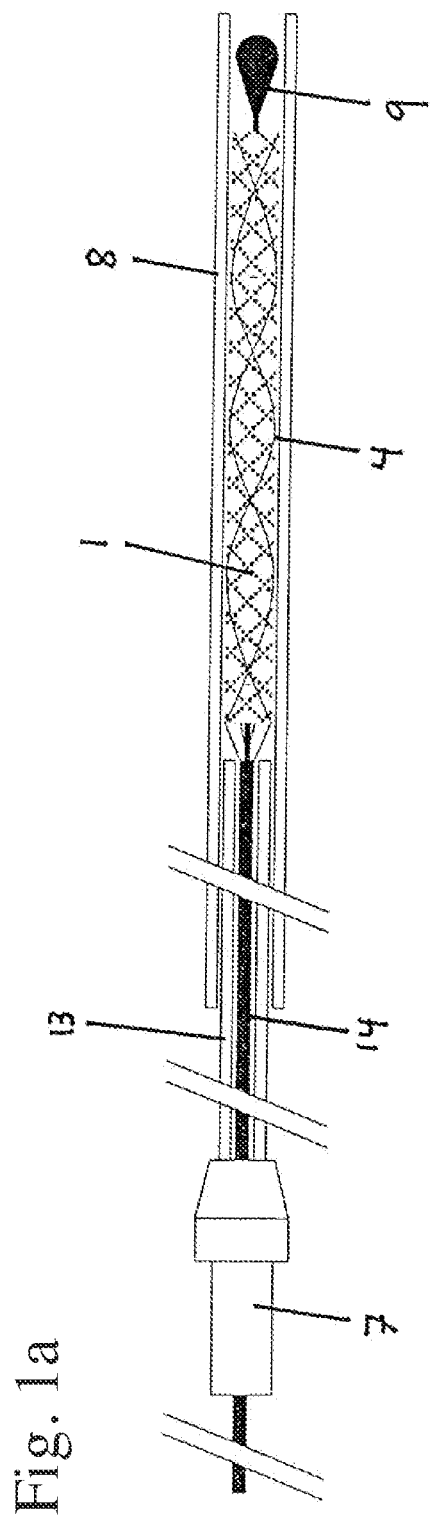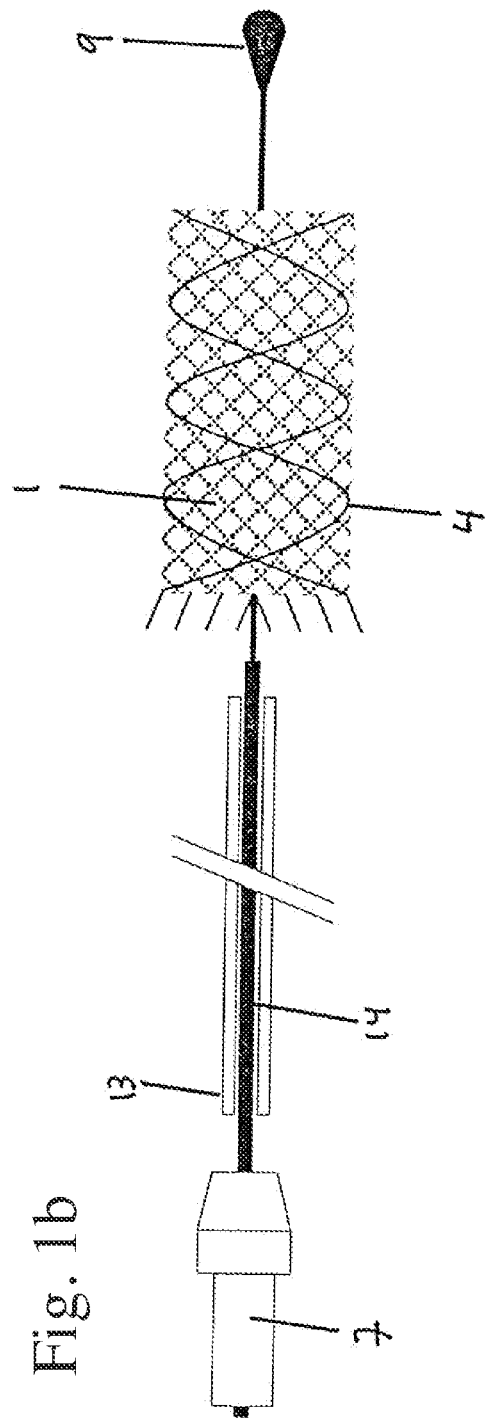

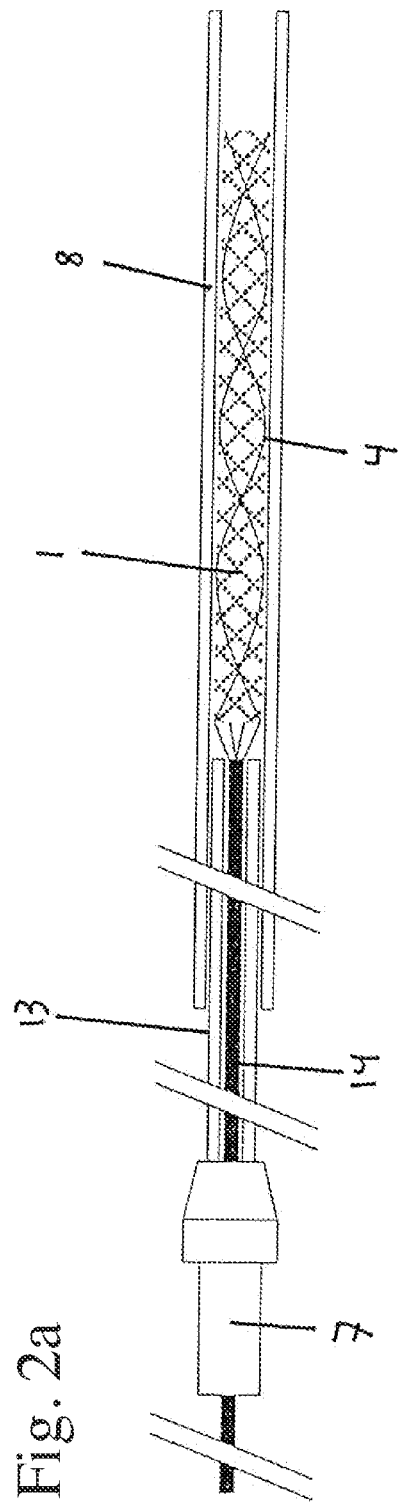
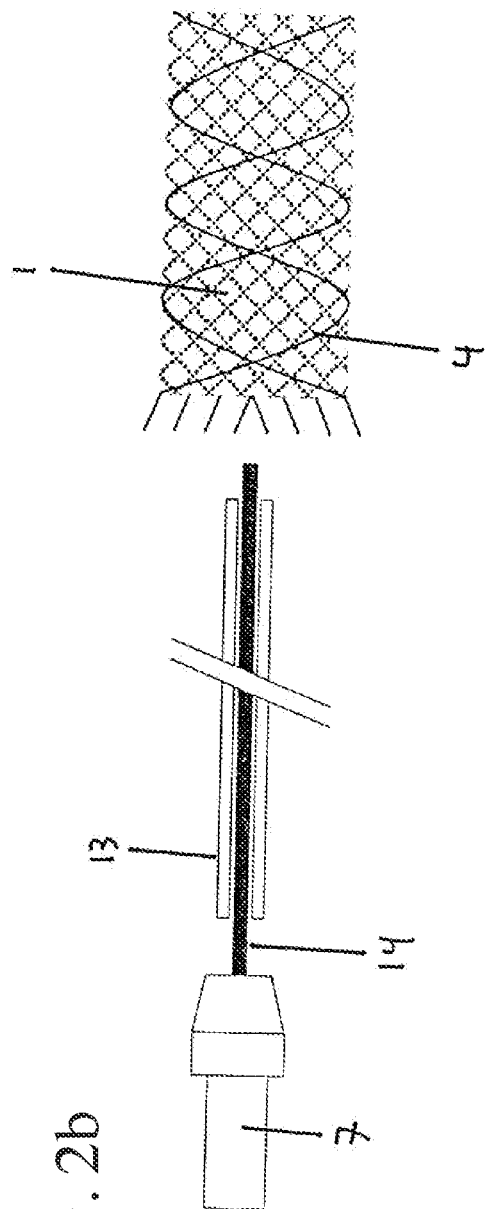

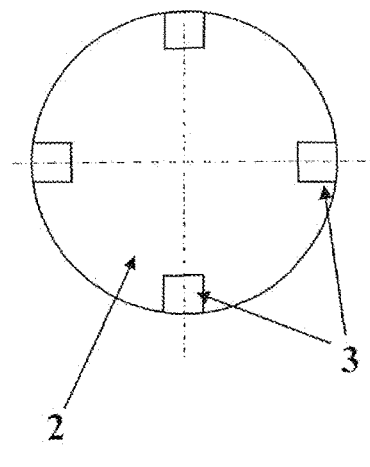
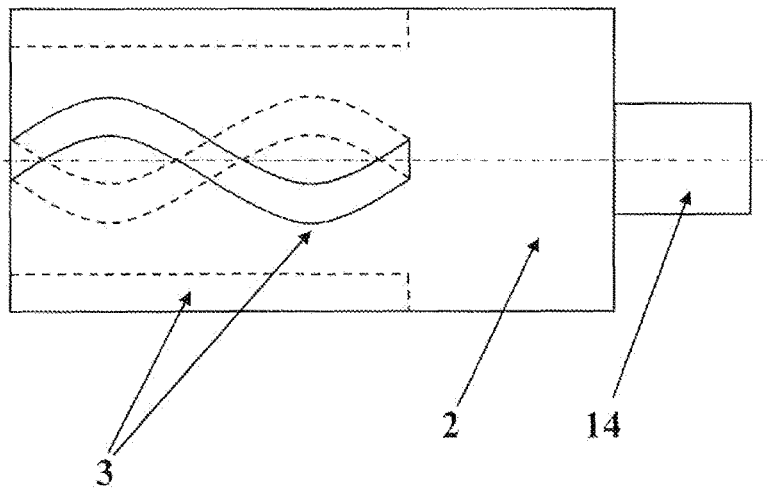
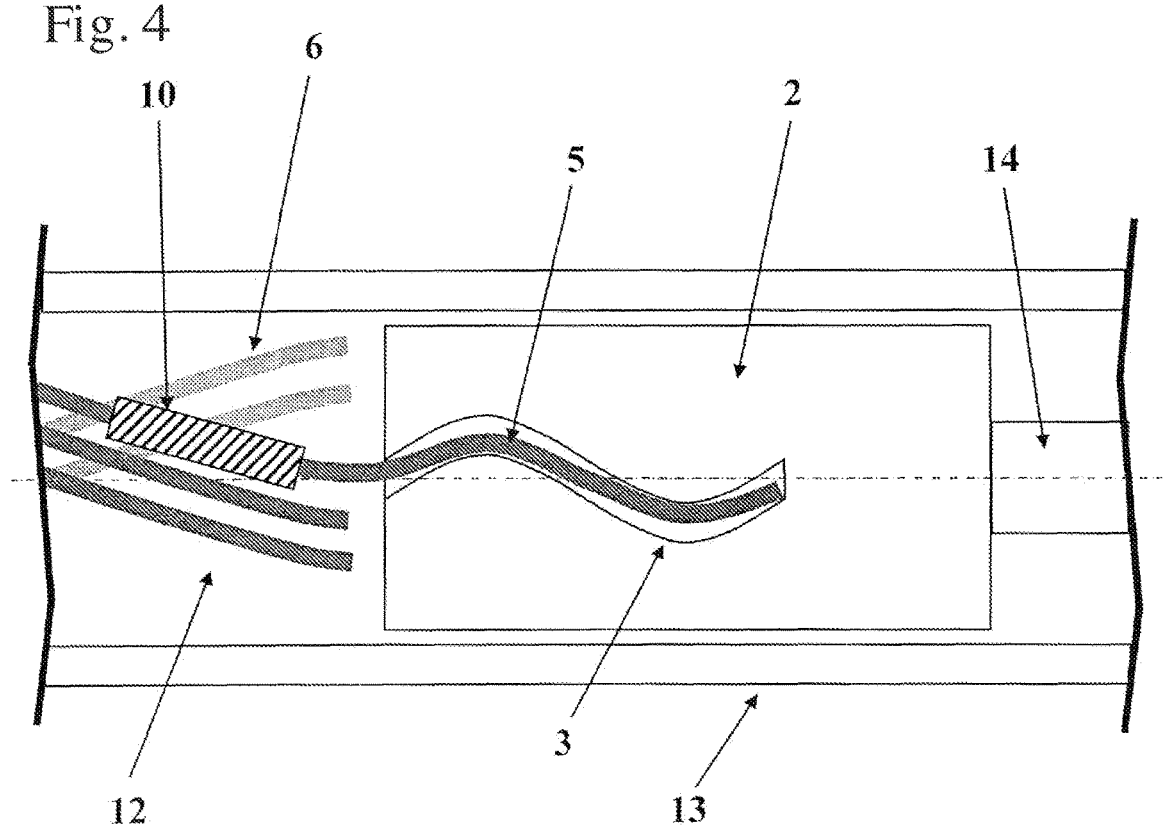

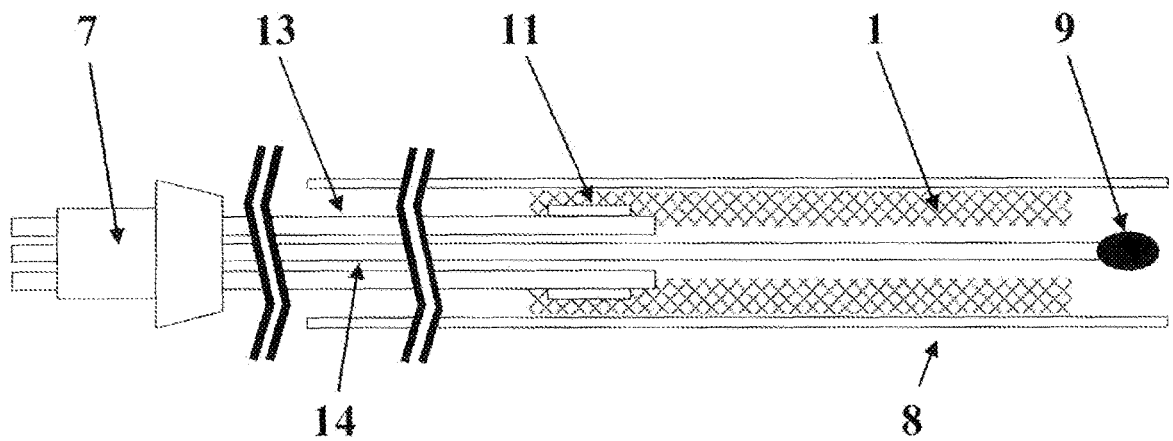
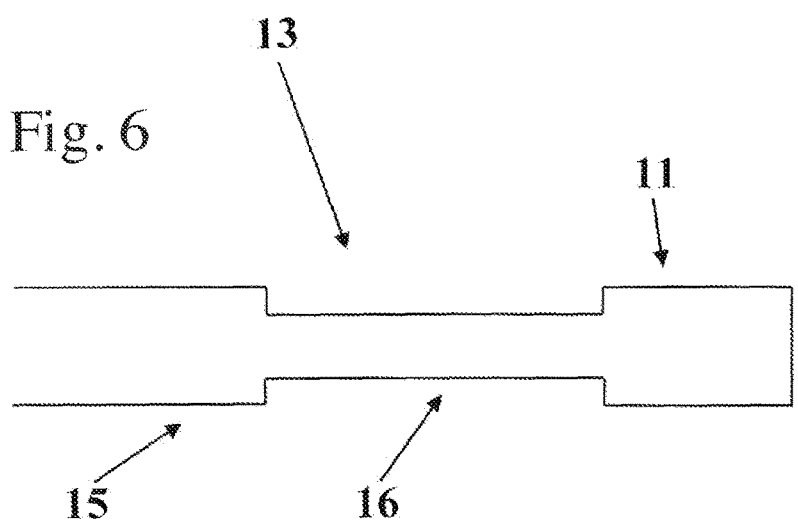
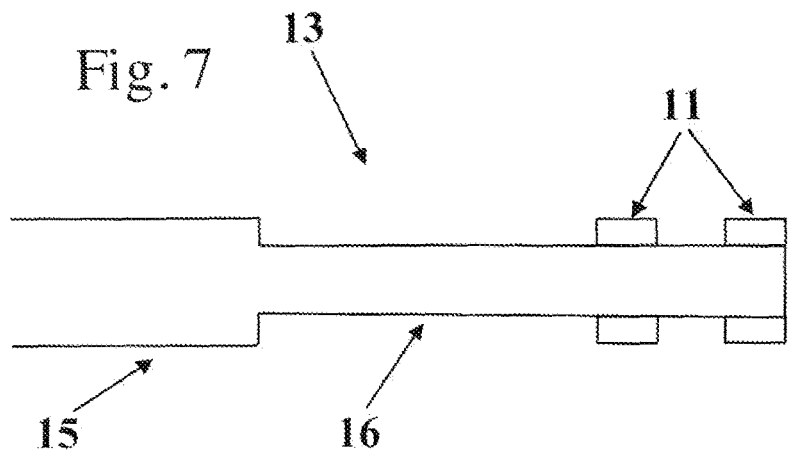

IMPLANT INSERTION SYSTEM

This application is a continuation of U.S. application Ser. No. 15/555,738, filed Sep. 5, 2017, pending, which is a U.S. National Stage application of International Application PCT/EP2016/054692, filed Mar. 4, 2016, which claims priority to DE application 102015103240.6, filed Mar. 5, 2015.

FIELD OF THE INVENTIONS

The invention concerns a device for introducing an implant into blood vessels or hollow organs of the human or animal body, comprising an implant, an insertion wire and a release tube, wherein the implant is deformable so that it adopts a shape with reduced diameter in a microcatheter and at the site of the implantation it expands once the external constraint of the microcatheter disappears, adapting to the diameter of the blood vessel or hollow organ, wherein a holding element is arranged on the insertion wire. According to an alternative embodiment, the invention concerns a device for introducing an implant into blood vessels or hollow organs of the human or animal body, comprising an implant and a release tube, wherein the implant is deformable so that it adopts a shape with reduced diameter in a microcatheter and at the site of the implantation it expands once the external constraint of the microcatheter disappears, adapting to the diameter of the blood vessel or hollow organ, and the release tube has a lumen running in the longitudinal direction of the device, through which an insertion wire can be led in lengthwise mobile manner.

BACKGROUND OF THE INVENTIONS

Arteriovenous malformations in a patient may lead to substantial impairments and dangers, even to death. This holds in particular for arteriovenous fistulas and aneurysms, especially when they occur in the cerebral region. As a rule, one tries to close such malformations by implants. Such implants are usually placed in endovascular manner with the aid of catheters.

Especially in the case of aneurysms, the implanting of platinum spirals has proven to work well, which spirals fill up the aneurysm more or less entirely, block the inflow of blood for the most part, and result in the forming of a local thrombus, ultimately closing the aneurysm. However, this treatment method is only suitable for aneurysms having a relatively narrow access to the vascular system, so-called berry aneurysms. For outgrowths of blood vessels having a broad access to the vessel, the implanted spirals are liable to be flushed out once more and cause damage in other areas of the vascular system.

In such cases, it has already been proposed to install a kind of stent, which "bars up" the opening of the aneurysm and thereby prevents the flushing out of the occlusion spirals. But such stents which have a relatively wide-meshed wall have a number of drawbacks.

On the one hand, this is the wide-mesh structure which allows blood flow unimpeded into the aneurysm. But if the aneurysm is not sufficiently filled with the occlusion means, pressure remains undiminished on the vessel wall. Under these circumstances, a further treatment is only possible with difficulty, since the stent impairs the access to the aneurysm and hinders the emplacement of additional occlusion means.

Another drawback is the poor adaptability of the stent to its installation site. For an optimal function, the stent should be applied tightly to the vessel wall, yet without exerting excessive pressure on the wall. Contrary to stents which are supposed to bring about a widening of the vessel in event of stenosis, these stents are rather to be seen as a kind of cuff, which is supposed to influence the vascular lumen and the endothelial wall of the vessel as little as possible.

Stents consisting of wire braiding have long been known, in particular for use in the coronary region. These stents are generally made as a round braiding, the individual wire filaments forming the stent wall in oppositely directed spiral or helical layers. The result is a mesh braiding which both supports in the radial direction and also is permeable to the blood.

Such stents consisting of filaments as a round braiding when used for treatment of stenosis are often expanded hydraulically with the aid of a balloon at the installation site and secured to the vessel wall. During the insertion, the balloon secured to an insertion wire serves as a transport vehicle, on which the stent is crimped. But for implants serving to influence or channel the blood flow in the cerebral region, an implant which spontaneously adapts to the vessel diameter and lies against the vessel wall is of advantage.

WO 2008/107172 A1 describes an implant in which the braiding has an elongated shape with reduced diameter in a microcatheter and expands at the implantation site, adapting to the vessel diameter and increasing the braiding density, wherein the filament ends sticking out at the implant ends are brought together at least in pairs and joined to each other. In this way, an implant is provided which is able to adapt to the particular vessel diameter, wherein the filament ends are atraumatic.

According to this prior art, connection elements are arranged at the joined filament ends, interacting with holding elements by the lock and key principle. The holding element by which the implant is coupled to an insertion wire has recesses in which the connection elements are fitted. The connection elements have a thickening, such as a spherical shape, so that they are held by form fit in the recesses of the holding element. The fixation in the recesses can be done with the aid of a tube, which is pulled in form fitting manner over the holding element with the fitted-in connection elements. After reaching the end position of the implant, this tube is pulled back in the proximal direction, and the implant is released. After this, the insertion wire with holding element, tube and catheter can be pulled back and removed from the body.

The described prior art has basically worked well, but in certain cases it may happen that not all of the connection elements are released from the recesses of the holding element provided for them after retracting the tube, for example, because a skewing occurs and continues to hold a connection element in the recess of the holding element. In such a case, the implant does not open at its proximal end as quickly as desired, and might only become released from the holding element after further movement of the insertion wire. On the other hand, a release system is desirable in which the implant is released entirely from the holding element immediately after retracting of the tube and becomes free in this way. Thus, the problem which arises, starting from the prior art described in WO 2008/107172 A1, is to further optimize the release system.

SUMMARY OF THE INVENTIONS

This problem is solved according to a first embodiment of the invention by a device for introducing an implant into blood vessels or hollow organs of the human or animal body, comprising an implant, an insertion wire and a release tube, wherein the implant is deformable so that it adopts a shape with reduced diameter in a microcatheter and at the site of the implantation it expands once the external constraint of the microcatheter disappears, adapting to the diameter of the blood vessel or hollow organ, wherein a holding element is arranged on the insertion wire and the holding element has at its periphery at least one, preferably a plurality of grooves set into the holding element, running along the circumference of the holding element and forming tracks in the form of curved lines, wherein the implant has at the proximal end at least one, preferably a plurality of holding wires extending in the proximal direction, which are fitted into the grooves, wherein the release tube is pulled with a form fit over the holding element and the holding wires fitted into the grooves, so that the holding wires are held in the grooves by frictional locking and a releasing of the implant occurs by pulling back the release tube in the proximal direction. The release tube constitutes a tubular sheath for the grooves of the holding element and the holding wires inserted into the grooves.

According to the invention, the holding element thus has grooves which are set into the holding element radially on the outer side of the holding element. The grooves are such that holding wires extending proximally from the implant can be inserted into the grooves. The holding wires generally extend proximally across the implant itself. In order to make possible both an advancement of the implant in the distal direction and a retraction in the proximal direction with the help of the insertion wire, without the implant becoming detached from the holding element, the grooves have a curved course on the outer side of the holding element. In the event of a straight course of the grooves in the longitudinal direction of the device, the danger would exist of pulling the holding wire of the implant out from the grooves upon retraction of the insertion wire. Furthermore, the dimensions of the grooves and the holding wires should be attuned to each other, so that the frictional forces between the grooves and the holding wires which prevent a releasing of the implant are greater than the pulling or pushing forces arising during the retraction or advancement of the insertion wire. In particular, the cross section of the grooves should only be slightly larger than the cross section of the holding wires, so that on the one hand after retraction of the release tube an expanding of the implant in the radial direction is easily possible for the purpose of a releasing, but on the other hand the frictional forces between grooves and holding wires are large enough so that a pulling of the holding wires out from the grooves in the axial direction can only occur with disproportionately large expenditure of force.

Unlike the previously described prior art, in which the connection of connection element and holding element relies on form fitting, according to the invention the securing of the holding wires in the grooves provided for them is based on frictional fitting or force fitting. The frictional forces between the holding wires and the grooves are so large that a releasing by action of force in the axial direction, i.e., the longitudinal direction of the device or also the insertion wire or implant, is virtually impossible in practice. But if the release tube is pulled back so far that the grooves are exposed radially, the implant can expand, wherein at the same time the holding wires move radially outward from the grooves. In this way, a releasing of the implant from the holding element is assured; the implant is thus finally released and implanted at the intended site. After this, the insertion wire plus holding element connected to it, the release tube as well as the microcatheter can be retracted and removed from the body.

For the emplacement of the implant, first of all with the help of the insertion wire the implant is advanced through the microcatheter up to the desired position. The holding element and usually the entire insertion wire are surrounded by the release tube in this process. As soon as the releasing of the implant should occur, at first the microcatheter is pulled back. Yet this by itself does not yet cause a final releasing, since the release tube continues to ensure that the holding wires emerging from the implant are still held in the grooves of the holding element. The grooves are arranged in the outer region of the holding element; thus, due to the expanding of the implant after its releasing from the microcatheter, there is a natural tendency for the holding wires to move outward and be released from the grooves. However, this is only possible if the release tube also has been pulled back. The treating physician thus has sufficient time after retraction of the microcatheter to judge the situation and either bring about the final releasing of the implant by pulling back the release tube in the proximal direction or, if the emplacement of the implant did not occur as desired, to move the implant back into the microcatheter by pulling back the insertion wire and implanting it in a different location, or also to remove the device once more from the body. Once the implant has been successfully released at the correct position, the insertion wire with the holding element and the release tube can be retracted into the microcatheter and removed together with it from the blood vessel system.

In the context of the description, by the term proximal shall be meant turned toward the treating physician, i.e., the proximal end points in the direction of the exterior of the body. On the other hand, distal means turned away from the physician, i.e., the distal end lies in the direction of the interior of the body.

Typically, the release tube extends from the holding element, whose grooves must be covered in order to securely hold the holding wires in the grooves, proximally to outside the body. But it is also conceivable for the release tube not to cover the entire insertion wire, it being sufficient for the release tube to extend across the grooves of the holding element. In this case, the retracting of the release tube is done by a second wire or thread, which runs parallel to the insertion wire and proximally from the release tube in the proximal direction.

In order for the frictional forces between grooves and holding wires to be large enough, wave-shaped tracks for the grooves on the circumference of the holding element are advantageous. For example, the grooves can run in sinusoidal manner. Typically, the grooves run forming a curved, especially a wave-shaped track on the outside of the holding element, from proximal to distal direction, wherein the grooves need not extend over the entire length of the holding element. In particular, a plurality of wave-shaped grooves may run from proximal to distal direction and distributed over the circumference of the holding element, the wave-shaped grooves being arranged substantially parallel to each other. It is also conceivable for the wave-shaped grooves to run not only in the longitudinal direction, i.e., from proximal to distal direction, but also in a spiral in the longitudinal direction about the holding element.

Advisedly, a plurality of grooves for the holding wires are arranged in the holding element, especially at least 4 grooves. Preferred is a number of at least 8, especially 8 to 32 grooves. This ensures that the implant is held uniformly across its circumference and is detached uniformly from the holding element after retraction of the release tube. The holding element can be made for example from refined steel or a nickel-titanium alloy such as nitinol.

The implant itself is typically a braiding made from a plurality of braiding wires, which run in a spiral or helix, wherein contrary running braiding wires mutually intersect and form a mesh braiding. Such braiding structures are sufficiently well known from the prior art, such as WO 2008/107172 A, already cited above. However, it is also conceivable for the implant to be a tubular or sliced implant, where holding wires for fitting into the grooves of the holding element are arranged at the proximal end.

In the case of an implant which is assembled from a wire braiding, it is advisable to use the proximal sections of the braiding wires forming the implant as the holding wires. For this, individual braiding wires may be lengthened in the proximal direction. For example, every second, every fourth or every eighth braiding wire can be formed longer at the proximal end, this lengthening of the braiding wire in the proximal direction constituting the proximal section, otherwise called the holding wire. This holding wire is placed in a groove provided for this purpose. In the case of an implant consisting of 64 braiding wires, for example, every second braiding wire can be formed longer at the proximal end, so that in all there are 32 holding wires and 32 grooves must be provided for them in the holding element. It is likewise possible to form only every 4th braiding wire longer (in the case of 64 braiding wires there are thus 16 holding wires and 16 grooves) or every 8th braiding wire (in the case of 64 braiding wires there are thus 8 holding wires for 8 grooves).

Moreover, it is advisable for the release tube prior to the retraction in the proximal direction for the releasing of the implant to cover not only the holding element and the holding wires fitted into the grooves, but also the proximal end of the implant itself. Thus, the release tube also covers the shorter proximal ends of the braiding wires, which are not lengthened in the proximal direction for the purpose of forming the holding wires. These proximal ends of the braiding wires not lengthened into holding wires are typically loose, but are also covered by the release tube. The advantage of such a configuration is that even after the implant is pushed out from the microcatheter or the microcatheter is retracted, so that the implant is basically lying free, a retracting of the implant into the microcatheter is still possible, as long as the release tube covers the holding element as well as the holding wires fitted into the grooves of the holding element. Even though the greater portion of the implant can expand radially after the retraction of the microcatheter, this does not apply to the proximal end of the implant, as long as the release tube is slipped over onto it. If no expansion has occurred as of yet at the proximal end of the implant, a retracting of the implant into the microcatheter is possible, in which case the already expanded regions of the implant once again fold up tightly.

According to another advantageous embodiment, the holding wires are deformed so that the frictional forces between the holding wires and the grooves are increased. This further improves the secure placement of the holding wires in the grooves and ensures that an unintentional pulling of the holding wires out from the grooves is virtually impossible. For example, a two or three-dimensional shape can be given to the holding wires, which prevents the holding wires from sliding out of the grooves under a tensile stress. Such a two or three-dimensional structure can be produced, for example, by machining or heat treatment.

According to a second embodiment, a simplified release system is likewise provided, based on frictional locking (force locking). This embodiment concerns a device for introducing an implant into blood vessels or hollow organs of the human or animal body, comprising an implant and a release tube, wherein the implant is deformable so that it adopts a shape with reduced diameter in a microcatheter and at the site of the implantation it expands once the external constraint of the microcatheter disappears, adapting to the diameter of the blood vessel or hollow organ, and the release tube has a lumen running in the longitudinal direction of the device, through which an insertion wire can be led in a lengthwise mobile manner, wherein the release tube protrudes into the proximal end of the implant and an elastic contact surface is present between the inside of the implant and the outside of the release tube, so that a frictional locking is generated between implant and release tube, bringing about a lengthwise mobility of the implant inside the microcatheter by lengthwise movement of the release tube distally or proximally.

Unlike with the previously described embodiment, the release tube does not encircle the proximal end of the implant or the holding wires emerging from the implant, but instead protrudes into the latter. A frictionally locking connection is produced between release tube and implant, so that it is possible, by advancing or retracting the release tube, to move the implant in the same way distally or proximally. The frictional locking between release tube and implant is brought about in that the portion of the release tube protruding into the implant has an at least partly elastic contact surface. Preferably this involves an intermediate layer, which is present on the outside of the release tube in the portion of the release tube protruding into the implant and which can also be called a pad. The elastic contact surface, preferably the intermediate layer, ensures a frictionally locking connection with the implant. Such an embodiment is especially easy to construct and requires no forming of additional elements on it to bring about a form fit.

The releasing of the implant occurs in that the implant is pushed out from the microcatheter or the microcatheter is retracted proximally relative to the implant. Since the implant has a natural tendency, after disappearance of the external constraint due to the microcatheter, to expand radially, the implant after being released from the microcatheter is detached from the elastic pad and lies against the inner wall of the vessel or hollow organ. The release tube, the microcatheter and optionally the insertion wire running through the release tube can then be retracted and removed from the body.

The release tube has an internal lumen through which the insertion wire can extend. Typically, after the insertion wire has been placed in the desired position, the microcatheter is pushed via the insertion wire up to the target site. After this, the release tube and the implant frictionally joined to it can be advanced distally through the microcatheter. The retraction and removal of the insertion wire is possible before, during, or after the releasing of the implant. If one wishes to prevent the insertion wire tip from moving into distally situated vessels, a retraction of the insertion wire can occur already before or during the releasing of the implant.

The elastic contact surface/intermediate layer typically runs in a ring around or encircles the release tube. In other words, the release tube is surrounded in radially encircling manner in one region by the elastic contact surface/intermediate layer, which ensures the frictionally locking connection to the implant. The implant is typically a braiding made from braiding wires, although other kinds of implants are not precluded, such as tubular or sliced implants.

In order to produce the frictionally locking connection with the implant, one or more intermediate layers (pads) can be provided, wherein the pads may extend for a certain length inside the implant. As a rule, the number of pads will be 1 or 2, wherein in the case of using two pads these may be configured correspondingly shorter. At the place where the intermediate layers are arranged on the release tube, the latter has a larger outer diameter than in the adjoining regions without intermediate layer.

The material used for the intermediate layer/pad must be elastic, in order to produce sufficiently large frictional forces between release tube and implant which make possible the advancement or retraction of the implant via the release tube, without the implant moving relative to the release tube in the longitudinal direction or even being detached from the release tube. Many different materials may be considered as materials for the elastic intermediate layer, in particular it may be an elastomer. For example, rubber, India rubber, or silicone may be used.

The intermediate layer may also be made from a polymer material such as polytetrafluoroethylene, polyester, polyamides, polyurethanes or polyolefins. Especially preferred are polycarbonate urethanes. The intermediate layer is preferably produced by electrospinning. In this process, fibrils or fibers are deposited from a polymer solution with the help of electric current onto a substrate. During the depositing, the fibrils stick together to form a fleece. As a rule, the fibrils have a diameter of 100 to 3000 nm. Layers produced by electrospinning are very uniform, tough, and mechanically durable. In regard to the creation of an intermediate layer by means of electrospinning, we refer in particular to WO 2008/049386, DE 28 06 030 A1 and the literature cited therein.

It is likewise possible to make the intermediate layer from the same material as the release tube, which preferably consists of a polyimide. In this case, the intermediate layer can be formed as a single piece with the release tube, wherein the release tube has a correspondingly larger outer diameter in the region of the intermediate layer than in adjoining regions of the release tube without an intermediate layer. According to the invention, an intermediate layer formed as a single piece with the release tube is also covered by the term intermediate layer, as long as the intermediate layer is elastic and produces a sufficiently large frictional locking with the implant. It is also possible for the release tube to have a uniform cross section in the section in which the implant extends, as long as a sufficiently strong frictional locking is generated between implant and release tube. For example, a distal section of the release tube can also have a reduced diameter, so that this distal section can be introduced in the longitudinal direction into the implant in order to produce here the desired frictionally locking connection.

Radiopaque material can additionally be provided between the elastic intermediate layer and the actual release tube, in order to improve the visualization of the implant installation process. Especially preferable is a coil of radiopaque material, as this is sufficiently bendable to ensure a problem-free advancement of the implant. However, radiopaque material of another form is also possible, such as in the form of a sleeve placed on the release tube. Preferred radiopaque material is platinum and platinum alloys. In particular, the elastic intermediate layer can be provided with a polymer layer, preferably one of polycarbonate urethane, especially preferably made by means of electrospinning, as described above.

According to another variant of the second embodiment, a release wire is wound around the implant in the region where the release tube protrudes into the proximal end of the implant and in which an elastic contact surface is present between the inside of the implant and the outside of the release tube, so that the release wire produces a strengthening of the frictional forces between implant and release tube, wherein the release wire is electrolytically corrodible.

According to this variant, the implant is not held in a compressed form by the microcatheter, or not solely by it, but rather (also) by a release wire, which is wound around the implant as well as the release tube with elastic contact surface introduced into the implant. The release wire is, as it were, tightly laced on the implant. Thus, as long as the release wire is not loosened, no final releasing of the implant can occur, because the frictional forces between implant and release tube are too large. For the producing of large frictional forces, the release tube has elastic contact surfaces, preferably elastic intermediate layers/pads as described above. But unlike the previously described variant, the implant is also still held by frictional locking on the release tube when the microcatheter has already been retracted from the implant or the implant has been pushed out from the microcatheter. In this way, an especially good security is ensured in the emplacement of the implant, since even after the releasing of the implant from the microcatheter the implant still remains at first in its compressed shape and therefore a retraction of the implant into the microcatheter continues to be possible.

The release wire surrounds the implant in the axial position where the elastic contact surfaces, preferably the elastic intermediate layers/pads, are located. The release wire can be tied around the implant directly where an elastic contact surface or pad is located. A tying around the implant is also possible in an axial position of the implant situated between two elastic contact surfaces or pads.

The release wire wound around the implant is electrolytically corrodible at least at one release site. This release site should be located in the section of the release wire which is placed in the form of a loop or winding about the implant. Instead of an electrolytic corrodibility, a thermal detachment is also conceivable, in which case the release site is heated so much that the release wire is severed. The electrolytic corrosion or also the heating is brought about by applying a voltage source. For this, the ends of the release wire are preferably led proximally to a point where the connection can occur. In other words, the release wire runs proximally to the position of the release tube introduced into the implant, forms there a loop or winding about the implant, and then runs back in the proximal direction. When a voltage is applied to the release wire, an electrolytic corrosion of the release wire occurs at the release site, so that the release wire is severed at this position. Thus, the release wire is no longer able to press the implant against the release tube. On account of the tendency of the implant to expand after disappearance of an external constraint, the implant is detached from the release tube and thus finally released. Microcatheter, release tube, insertion wire and release wire can then be retracted.

In order to bring about an electrolytic corrosion of the release wire, it may be advisable to weaken the release wire at least at one position so that the electrolytic corrosion occurs preferably at this release site. This release site may have, e.g., a smaller cross section than other regions of the release wire. Furthermore, it is possible to make portions of the release wire from a material which dissolves especially well when an electric voltage is applied. The materials which can be used for the release site correspond to those which are also used, for example, in electrolytically detachable implants. These include steel, magnesium or magnesium alloys as well as cobalt-chromium alloys. The latter are described in WO 2011/147567 A1, to which reference is made in this regard. In order to achieve a concentration of the current flow at the release site, the release wire can be insulated partly or entirely by a jacketing outside of the release site.

In the described variant with release wire, for the introducing of the implant one proceeds by advancing the implant, secured on the release tube, through the microcatheter to the target site by moving the release tube distally. The frictionally locking connection between release tube and implant ensures that the implant moves along with the release tube accordingly. At the target site, the microcatheter is retracted proximally or the implant is pushed out distally from the microcatheter. Thanks to the lacing with the release wire, the implant continues to be held on the release tube until the treating physician decides on the final releasing of the implant. For this, a voltage is applied to the release wire, whereupon it is severed and releases the implant to expand.

The principle described here of a release wire which surrounds the implant in the position in which the release tube is introduced by its elastic contact surfaces into the implant so that the frictional forces between implant and release tube are increased until a lengthwise movement of the implant is possible by advancement and retraction of the release tube can also be applied to an embodiment in which the insertion wire itself, rather than a release tube, has elastic contact surfaces, especially elastic intermediate layers or pads. In this case, therefore, a frictional locking is not produced between implant and release tube, but instead between implant and insertion wire. This enables an advancement of the implant by advancement of the insertion wire through the microcatheter. One may omit a release tube surrounding the insertion wire in this case. Such an embodiment is also included in the invention.

The producing of a frictionally locking connection between implant and insertion wire (instead of the release tube) also constitutes a third embodiment according to the invention which is covered by this application, i.e., without the presence of the above-described release wire. For this, an elastic contact surface is provided on the insertion wire, especially one in the form of an elastic intermediate layer or an elastic pad, which increases the frictional forces between implant and insertion wire so much that a movement of the implant is possible by advancement or retraction of the insertion wire. In this case, the use of the above-described release tube is unnecessary.

The elastic intermediate layer or elastic pad in this variant of the invention is preferably made of polycarbonate urethane, especially by means of electrospinning. This method has already been described above.

In particular, according to the third embodiment of the invention in which the frictionally locking connection is produced between insertion wire and implant, a coil as it is customarily called in medical technology can be arranged on the insertion wire, the coil being coated with an elastic material. This may involve the aforementioned elastic materials: rubber, India rubber, or silicone, or also polymer materials such as polytetrafluoroethylene, polyester, polyamides, polyurethanes or polyolefins. Especially preferred are polycarbonate urethanes. The elastic material thus forms the intermediate layer. When using the mentioned polymers, especially when using polycarbonate urethane, once again an application by means of electrospinning is possible, as mentioned in connection with the above embodiments.

The coil itself is preferably made of a radiopaque material, preferably platinum or a platinum alloy, which makes possible a visualization of the implanting process. At the same time, however, the coil is sufficiently bendable, so that the insertion wire with the implant placed thereon can also easily follow narrow-lumen blood vessels during its advancement. In principle, it is also possible to place radiopaque material on the insertion wire in a different form, such as a metallic sleeve, although in this case the bendability is less than in the case of a coil.

The following remarks, unless otherwise emerges from the context, refer to both the first and also the second and third embodiment of the invention as described above. Basically, all of the features which are mentioned in the course of this description in connection with the first, second, or third embodiment can also be features of the other respective embodiments, unless otherwise specified by the context or unless technically impossible.

According to a preferred embodiment, the outer diameter of the release tube varies between proximal and distal end, wherein the variation of the outer diameter pertains to the regions of the release tube not surrounding the holding element or situated outside of the implant. These latter mentioned regions shall be called hereinafter the distal section. By a variation of the outer diameter of the release tube between proximal and distal end, the benefits of good flexibility and an easy, predictable detachment are combined with each other. In partial sections of the release tube, especially in a region which is proximally adjacent to the distal section, directly surrounding the holding element or engaging with the implant, a good flexibility is of special importance so that the overall device when introduced can even follow along fine vessel bends. For this reason, a small outer diameter makes sense here. On the other hand, the further proximally situated sections of the release tube should have an adequate resistance to an unwanted lengthening. This is of special importance in the proximal section, since this accounts for the greater portion of the overall length of the release tube, and therefore its stretchability in the longitudinal direction should be the least possible, or else an unwanted large overall distension may occur along the overall length. A greater resistance to an unwanted lengthening can also be of advantage in the distal section itself, which according to the first embodiment of the invention surrounds the holding element, so that this section of the release tube in fact moves proximally during the retraction and does not merely stretch in the longitudinal direction. For this reason, the distal section may also have a larger outer diameter than the middle section, but that is not absolutely necessary. The desirable outer and inner diameter in the distal section also has to do with the dimensions of the surrounded holding element.

Accordingly, a release tube is advantageous with a distal section which surrounds inter alia inter alia the holding element (first embodiment of the invention) or extends into the implant (second embodiment of the invention), a middle section following this in the proximal direction with small outer diameter, and a section with large outer diameter following the middle section in the proximal direction. Furthermore, it may be advisable for the distal section to also have a large outer diameter in order to enclose the holding element with the holding wires fitted onto it. In other words, the section which covers the grooves in the holding element has a large outer diameter and thus a greater stiffness than the middle section following it in the proximal direction, whose flexibility is of particular importance for the introducing of the device. The by far longest section, which is called here the proximal section, in turn has a large outer diameter in order to make possible an inserting and retracting of the release tube even over relatively long distances.

Typically the length of the middle section is 50 to 500 mm, especially 80 to 120 mm, especially preferably around 100 mm. The distal section may have a length of 2 to 10 mm; this is generally enough to cover grooves in the holding element. The overall length of the release tube can be 1000 to 2000 mm, e.g., 1800 mm, and accordingly the proximal section is normally the longest and has a length of 500 to 1900 mm.

The expressions "large outer diameter" and "small outer diameter" are to be understood according to the invention as meaning that in regions with large outer diameter the outer diameter is larger than in regions with small outer diameter. The precise dimensions may vary, as can the ratio of the diameters, especially in dependence on the conditions in the blood vessel system and the particular purpose of the implanting. But a typical large outer diameter lies in a region of 0.4 to 0.8 mm, especially 0.5 to 0.7 mm, such as around 0.6 mm. A typical small outer diameter is 0.3 to 0.55, especially 0.4 to 0.5, such as around 0.45 mm.

The proximal section of the release tube with generally large outer diameter may be followed by yet another proximal end, which in turn has a relatively small outer diameter. The release tube here is advisedly clamped on the insertion wire, e.g., with the aid of a torquer, in order to produce a frictional locking and prevent an unwanted mutual displacement of insertion wire and release tube. When using the implant according to the first embodiment of the invention, a displacement should only occur when it is necessary to release the implant.

In order to facilitate the retracting of the release tube for purposes of releasing the implant, a grasping feature may be provided at the proximal end of the release tube, regardless of the outer diameter in this region. This may be in the form of a thickening or a sleeve enclosing the proximal end of the release tube. When the releasing of the implant is supposed to occur, the torquer which clamps the release tube on the insertion wire is typically loosened and possibly placed again on the insertion wire in order to make it easier to handle. The release tube can then be grabbed by the user at the grasping feature and retracted in the proximal direction.

The passage of the implant plus insertion wire and surrounding release tube through the catheter can be facilitated by providing a coating of the release tube on the outside, which reduces the friction between release tube and catheter. This is preferably a hydrophilic coating.

When retracting the release tube it is furthermore advisable to maintain the frictional forces between insertion wire and release tube as low as possible. For this, a friction-reducing coating can be used on the outside of the insertion wire or the inside of the release tube, at least in partial sections. The use of polytetrafluoroethylene (PTFE) is preferable. This holds especially for regions in which the insertion wire has been grinded, as is typically the case at the proximal end, in order to enable the grasping by means of a torquer.

Besides the outer diameter, the wall thickness of the release tube may also vary, i.e., in the regions with large outer diameter the release tube has a greater wall thickness than in the regions with small outer diameter. Reducing the wall thickness further increases the flexibility and bendability of the release tube, so that it can especially easily follow along fine branches of the blood vessel system inside the microcatheter.

The release tube can be produced by starting with a uniformly constructed release tube having a constant outer and inner diameter for at least the greater portion of its length, i.e., also a constant wall thickness. Material is removed from this release tube on the outside in the desired sections, thus decreasing the outer diameter. Since no material is removed on the inside, the wall thickness of the release tube is decreased to the same extent. One thus obtains a release tube as a single piece, wherein in partial sections, especially the middle section, the outer diameter as well as the wall thickness have been decreased by removal of material. In other partial sections, such as the proximal and possibly the distal section, usually no material is removed, i.e., the original outer diameter remains intact here.

The removal of material can be done with methods which are basically known from the prior art, such as lathe turning, grinding, or shaving off with the aid of mechanical tools or also with the aid of a laser. Material can also be removed at the proximal end, in order to enable the grasping by a torquer here.

The release tube is typically made from a plastic. Especially well proven are polyimides. However, the use of other materials is also conceivable, such as polypropylene or polytetrafluoroethylene (PTFE). Combinations of different plastics or multilayered, coextruded polymers can also be used. Furthermore, the release tube may also additionally have a reinforcement, in that fibres, for example metal fibers, may be embedded in the release tube. For example, a release tube strengthened by a fabric or braiding is conceivable.

In addition, the release tube can also be made of metal, in which case the release tube should be thin-walled in order that the bending stiffness is not too large. In particular, nickel-titanium alloys such as nitinol are attractive as the metal.

The mentioned materials can be used for the release tube regardless of whether it is a release tube of the first or second embodiment of the invention and whether or not the outer diameter of the release tube varies.

In order to further decrease the bending stiffness, the release tube may have recesses or material thinning, for example in the form of slots or openings. This holds regardless of the material used to make the release tube, i.e., both for plastics and for metals. The recesses or material thinning may be provided especially in certain regions of the release tube where a slight bending stiffness is of special importance, such as the distal region, or also be arranged over the entire length of the release tube. The flexibility of the release tube is increased in this way, but without adversely affecting the tensile strength.

The removal of material may be done in such a way that the release tube after the machining has a plurality of different outer diameters. In particular, the transition from sections with large outer diameter to sections with small outer diameter and vice versa may be gradual, for example, over several small stages, each of them having slightly different outer diameters. Likewise, a continuous transition is possible, so that the outer diameter evenly decreases or increases. In this case, the transition is conical. Viewed in a longitudinal cross section, the wall of the release tube may have a bevel or also a round or slanting or curved course at the locations of the transition from large to small outer diameter.

Alternatively, the release tube may also be in several pieces. In this case, partial sections of the release tube with different outer diameters are joined together, generally by integral bonding. A connection of the partial sections by adhesive is advisable.

When connecting the partial sections with different outer diameters the partial sections should overlap, in order to ensure a firm connection, especially a sufficient adhesion surface for the adhesive. Possibly the inner diameter of a partial section with larger outer diameter can be widened to make possible the partial inserting of a partial section with smaller diameter. In addition, it may be ensured that the transitions between the partial sections are as uniform as possible and that the outer diameter does not increase or decrease abruptly, but rather successively. For this purpose, the partial sections can be beveled; a material removal in a different way is also possible. It is likewise possible to apply a certain additional quantity of adhesive, for example, in order to achieve a continuous transition from large to small outer diameter.

The partial sections may also overlap over longer distances, for example, a layer of the release tube may run continuously over the greater portion of the length of the release tube. A layer is possible which begins at the distal end or slightly proximally to the distal end of the release tube and runs continuously to the proximal end and in this way assures a largely uniform inner diameter of the release tube. A uniform inner diameter is advantageous in terms of manufacturing technology. In certain sections, especially in the distal and proximal section, on the outside of the continuous layer of the release tube there is applied an outer layer of the release tube. The inner and outer layers are joined together, in particular by adhesive. Thus, at the place where inner and outer layer are joined together one obtains a release tube with larger outer diameter and greater overall wall thickness, but in the sections where no outer layer is present the outer diameter and the wall thickness are smaller. Surprisingly, it has been discovered that a multilayered construction also makes the sections of the release tube with large outer diameter more flexible, especially the proximal section. Thanks to the relatively large wall thickness and the associated large cross section surface of the outer wall, however, the tensile strength is high. Thus, as compared to a single-layer construction of the wall of the release tube, with the same overall wall thickness, the flexibility is greater, but the tensile strength is comparable.

Also in this embodiment the transitions between sections with large and small outer diameter can also of course be designed continuous or in the form of several small stages. Furthermore, the release tube can have further layers, besides the inner and outer layer, and thus the release tube can be constructed basically from as many layers as desired.

Regardless of the precise configuration of the release tube, the distance between the insertion wire and the inner wall of the release tube is significant, inasmuch as a bending or buckling may occur during the advancement in the microcatheter in event of too large a distance, i.e., too thin an insertion wire in relation to the inner diameter of the release tube, which in an extreme case will make further advancement impossible. On the other hand, too small of a distance between the inner wall of the release tube and the insertion wire is a problem, inasmuch as large frictional forces arise during relative movements, which may for example hinder the retracting of the release tube for purposes of releasing the implant.

It is advantageous for an inner layer of the release tube to run at least for the most part continuously from the distal to the proximal direction. By this is meant that the inner layer extends for at least 70%, preferably at least 80% and especially preferably at least 90% of the length. By the inner layer is meant here not only a layer which is at first separate and only afterwards joined to an outer layer, but also the inner portion of a single-piece release tube, as was described above. This results not only in a uniform inner diameter, but also largely avoids unwanted lengthenings of the release tube during the proximal retraction. On the one hand, the sections in which bendability is of special importance, especially the middle section, are especially thin and flexible, so that the release tube can be easily maneuvered through narrow blood vessels. On the other hand, other sections, especially the proximal and possibly the distal section, are sufficiently resistant to an unwanted lengthening of the release tube, when it is being retracted proximally. This ensures a secure and problem-free releasing of the implant.

The insertion wire may also have different diameters in different sections. In particular, the diameter may be smaller distally than in the proximal section, since a low bending stiffness is also advantageous for the insertion wire distally, so that it can follow in the best possible manner the course of the blood vessel inside the microcatheter. On the other hand, however, too small a diameter would make the insertion wire buckle during its advancement, making further advancement difficult if not impossible. It is therefore advisable to provide the insertion wire with a smaller diameter in the distal section, since the insertion wire is required to follow the course of the blood vessel especially in this place, while in the proximal section a problem-free advancement is more of a concern. The diameter can also vary repeatedly over the length of the insertion wire, preferably increasing or decreasing uniformly at the transitions in diameter. Thus, the transitions are preferably conical. The variation in diameter of the insertion wire can also occur independently of the variation of the outer diameter of the release tube.

While basically a lower diameter is advantageous in the distal section of the insertion wire, individual regions of the insertion wire may also in turn have a larger diameter in the distal section. This holds especially for the insertion wire tip. But in a partitioning of the insertion wire into a proximal and a distal half, it is advisable for the diameter in the distal half to be smaller on average than that in the proximal half.

The regions of the insertion wire with small diameter can be sheathed in a polymer, such as PTFE. In this way, a play between insertion wire and release tube is avoided, thereby preventing an unwanted deformation of the insertion wire during its advancement. Even so, the insertion wire remains sufficiently flexible and bendable in this section, because the polymer hardly stiffens the insertion wire at all. The polymer can also be provided in the form of a spiral coil entirely surrounding the insertion wire or only in partial regions. The spiral coil can also consist of another material, especially of metal.

It is advantageous for the outer diameter of the release tube and the diameter of the insertion wire to increase or decrease roughly in synchronized manner. This is also advisable in that a good flexibility is desirable in the same sections of the release tube on the one hand and the insertion wire on the other hand. Furthermore, this ensures that the distance between the inner wall of the release tube and the insertion wire remains relatively constant. The diameter of the insertion wire may decrease rather significantly distally, so that the inner diameter of the release tube can also be small in the corresponding sections; for example, it is possible for the release tube to have a smaller inner diameter in the middle section than the diameter of the insertion wire in the proximal section.

The insertion wire can also extend through the actual implant intended for releasing. In particular, the insertion wire can also extend distally beyond the distal end of the implant when the implant is in the compressed state. In other words, the insertion wire tip lies further distally than the distal end of the implant when the latter has not yet been released from the holding element. In this way, even after the releasing of the implant, an object still runs through the inside of the implant in the beginning, until such time as the insertion wire is retracted. This makes possible the further probing of the vessel or the implant, for example by leading a catheter along the insertion wire and the adjacent insertion wire tip. The catheter is moved in this way through the released and expanded implant. The insertion wire tip is only removed by the final retraction of the insertion wire.

The insertion wire tip can have a rotationally symmetrical design. The cross section can be round, oval, rectangular, or basically any other shape. Furthermore, it is advisable to make the insertion wire tip visualizable, e.g., by making the insertion wire tip itself at least partially from a radiopaque material and/or by the insertion wire tip having a radiopaque marker at its distal end. The insertion wire tip can be made of refined steel, nitinol, platinum, platinum/iridium, platinum/tungsten or other metals.

The insertion wire tip and the actual insertion wire can be made as a single piece, i.e., it is ultimately a continuous wire. But it is also possible to make the insertion wire tip and the insertion wire separately and only afterwards join them together. In this way, the advantageous properties of different materials may be combined with each other, for example, the actual insertion wire can consist of refined steel with good advancement capability, while the insertion wire tip can consist of a nickel-titanium alloy such as nitinol to increase the flexibility. The fabrication from the nickel-titanium alloy need not be confined to the insertion wire tip itself, but rather it may involve the entire distal section of the insertion wire. Thus, the insertion wire may have a proximal and a distal section, for example the proximal section being made from refined steel, and the distal section from a nickel-titanium alloy. The transition between proximal and distal section typically occurs approximately where the holding element is situated in the first embodiment of the invention. A distal section made from a nickel-titanium alloy also has the advantage of minimizing the risk of buckling ("kink resistance"). On the other hand, the use of a stiffer material such as refined steel is advantageous for the proximal portion of the insertion wire, because this allows a transmission of torques, which is advantageous to the advancement capability.

Thus, independently of or also together with the device disclosed in the context of the remainder of this specification for introducing an implant, the invention also concerns an insertion wire with a proximal section and a distal section, wherein the distal section is made from a nickel-titanium alloy, preferably nitinol, while the proximal section is made from a stiffer material, i.e., a material with higher modulus of elasticity (Young's modulus). In particular, the material for the proximal section may be refined steel, but also a Co—Ni—Cr—Mo alloy such as MP35N, MP35NLT or Elgiloy.

The term insertion wire is to be understood broadly and need not in every instance signify a classical wire. For example, elongated insertion aids with an internal cavity are also conceivable. In this case, the above discussed diameter of the insertion wire corresponds to the outer diameter. However, it is important that the insertion wire extend proximally far enough so that the treating physician can grab and move the insertion wire.

The implant intended for being released itself preferably has a wall consisting of individual intersecting filaments, forming a tubular braiding. The tubular braiding is usually a round braiding and has a circular cross section as seen from the proximal or distal end. But deviations from the circular shape are also basically possible, such as an oval cross section.

The filaments forming the braiding structure may be individual wires of metal, but it is also possible to provide litz wires, i.e., several wires of slight diameter which together form a filament and are preferably twisted together.

The implant shall be described below with the aid of a flow diverter, which is suited to influencing the blood flow in a vessel, so that arteriovenous malformations can be sealed off as much as possible from the blood flow. The malformations are usually aneurysms. The device according to the invention however is not confined to this and is basically also suited for other implants which are designed to be introduced into blood vessels and released there, such as traditional stents, which are supposed to provide a supporting function.

The implant may also serve for the sealing of vessels which need to be decoupled from the blood circulation, for example because they are supplying tumors. The implant, with optimal choice of the ratio between implant diameter and vessel diameter, should be able to adapt itself to the respective vessel diameter. In the region of enlargements and outgrowths, it should adopt at most its nominal diameter, i.e., the diameter which the implant adopts without the exercising of an external constraint.

The material for the implant may be in particular materials with high restoring force or spring action. These are especially materials with superelastic or shape memory properties, such as nitinol. Wires of different diameter may also be used for the individual filaments. In this way, the advantages and disadvantages of wires with different cross section can be combined and compensated. The cross section of the wires is round in most cases, but wires with oval or polygonal cross section or combinations thereof are also possible.

In any case, it is important that the implant on the one hand is able to assume a compressed form in order to be led through the microcatheter, and on the other hand to automatically expand when freed from the external constraint of the microcatheter and lie against the inner wall of the vessel at the site of implantation. It is also possible to make the implant from composite materials, such as platinum-jacketed nickel-titanium wires or nickel-titanium-jacketed platinum wires. In this way, the shape memory properties of the nickel-titanium alloy (nitinol) are combined with the radiopacity of platinum.

The diameter of the implant in the expanded state is typically between 2.5 and 5.0 mm. The length is 20 to 40 mm, for example.

The insertion wire can be made from refined steel or a shape memory material, especially a nickel-titanium alloy such as nitinol. In the case of insertion wires with varying diameter it is possible to both grind down the insertion wire from a single wire, i.e., to remove material in the regions of smaller diameter. However, it is also possible to join together several individual wires to form an insertion wire at the places where the diameter of the insertion wire changes. Different materials can be used for this. In particular, it is possible to provide an insertion wire made of refined steel with a tip made of a nickel-titanium alloy at the distal end or in general to fashion further distally situated regions of the insertion wire from a nickel-titanium alloy and further proximally situated regions from a material with greater modulus of elasticity, such as refined steel.

When the implant is serving as a flow diverter, it need not necessarily provide a supporting function, as is the case with typical stents. Instead, the implant serves primarily to channel the blood flow in the region of the malformations as a kind of inner cuff. For example, it should also prevent occlusion means placed in an aneurysm from being washed out into the blood stream. Furthermore, the inflow and/or outflow of blood in an aneurysm can be prevented.

The implants are typically made as a braiding of a plurality of filaments, the braiding in principle forming an endless tube. The particular required implant length can then be cut off from this endless tube. The individual filaments are therefore wound in a spiral or helix, wherein the individual filaments are introduced as a trellis, that is intersecting above and below one another. As a rule, the individual filaments are wound in two directions intersecting at a constant angle, for example, an angle of 90°. Preferred—in the stress-free normal state—are angles of more than 90°, especially 90 to 160°, referring to the angles which open out toward the axial ends of the implant. Such a steep winding of the individual filaments, if it is sufficiently tight, can result in a braiding with large surface density or surface coverage, which when stretched axially can be pulled apart to form substantially smaller diameters. When the stretching forces cease, and if the filament material has adequate restoring force, the braiding once again approaches the nominal diameter, i.e., the originally stress-free state, and expands, resulting in it tightly hugging the vessel wall at the place of implantation and a denser mesh structure against the wall. This also holds in particular in the region of vessel expansions. The surface coverage in the regions of a vessel expansion, such as an aneurysm, is thus greater than in adjoining regions of the vessel. In addition or alternatively, the surface coverage of the braiding can also be varied by the weaving technique adopted. For example, the implant can be woven more densely in the middle region, where the aneurysm is typically covered, than in the end regions, so that an extensive covering of the neck of the aneurysm is assured. On the other hand, a sufficient flexibility is guaranteed by a lesser surface density in the end regions. Vessel branchings (bifurcations) can be provided for in the implants by regions with a lesser mesh density, for example. The thickness of the filaments is typically 0.01 to 0.2 mm, especially 0.02 to 0.05 mm. Each individual filament may consist of a single wire or a litz wire of several individual wires assembled and preferably twisted together. The individual wires may have the same diameter or also different diameters. The wires may also consist of different materials (nitinol, cobalt-chromium alloys, platinum alloys). Wires made from a radiopaque material, for example, ensure the radiopacity of the implant.

In the braiding, the filament ends sticking out at the implant ends can be brought together at least in pairs and be permanently joined to each other. This can be done, for example, by welding, but also by mechanical clamping, twisting, soldering or gluing. A connecting of the filament ends can also be done by means of placing a sleeve over them. This sleeve can enter into an integrally bonded connection with the filament ends, for example, by welding, or also by crimping. An alternative is for the sleeve to be dimensioned so that thickenings located on the filament ends are prevented from slipping through the sleeve. Thus, the sleeve can move in the axial direction relative to the filaments, but it cannot be fully pulled off. Moreover, the sleeves may be able to move relative to each other in the axial direction. In this way, when the implant is compressed the sleeves do not come to lie one above the other, so that the implant has on the whole a lesser diameter.

The bringing together and connecting of the filament ends is especially important at the proximal end of the implant; it has been found that even free filament ends at the distal end of the implant are no problem. Even so, it is of course possible to also bring together and join the filament ends at the distal end of the implant.

It is also possible to bring together the filaments to form first braiding ends, which are in turn connected to form second braiding ends, as described in DE 10 2009 006 180 A1.

In this case, or additionally, the connected filament ends are formed atraumatically. In particular, the filament ends may have an atraumatic thickening distally and/or proximally, which is approximately spherical in shape, for example. The thickening can be formed from the filament end or arranged on the filament end by laser welding, brazing, gluing, crimping, or similar.

In practice, the emplacement of the implants according to the invention is done under X-ray control. For this reason, the implant and optionally also the insertion wire should comprise a radiopaque marker material, unless it is itself made from a radiopaque material. Such radiopaque materials are in particular tantalum, gold, tungsten and platinum metals, especially platinum alloys such as platinum-iridium or platinum-tungsten. These markers may be attached for example as marker elements in known manner to the filament ends, or else they can also be interwoven as marker filaments in the braiding structure of the implant. It is also possible to enclose individual filaments with a helix or wire made from a radiopaque material such as platinum. The helix or the wire can be welded, glued, or similar, to the filaments. Another option is the coating or ballasting of the filaments with a radiopaque material.

Also possible are radiopaque markings in the form of sleeves which enclose the assembled filaments. These sleeves may be welded or also crimped to the filament ends. The radiopaque sleeves may be identical to the aforementioned sleeves for holding together the filament ends and thus play a dual role. Furthermore, it is possible to provide a distal section of the insertion wire with a coil of radiopaque material, such as a Pt-coil. Preferably, this is arranged proximally adjacent to the holding element.

It is also conceivable to introduce radiopaque substances into the release tube. This may involve radiopaque particles, such as are typically used as contrast agents in X-ray technology. Such radiopaque substances are, for example, heavy metal salts like barium sulfate or iodine compounds. The radiopacity of the release tube is helpful for the introduction and localization of the implant and can be used in addition to or in place of marker elements.

As described above, for the closure of aneurysms in the stress-free arrangement of the individual filaments in the braiding, the implant surface should have the densest possible configuration. Since the flexibility of the braiding must remain intact, a 100% surface coverage by the filaments is, however, at best approximately possible. But depending on the application, even lower surface coverages result, or even lower surface coverages have proven to be adequate. Preferable is a surface coverage in the range of 30 to 80%, preferably 35 to 70%.

In order to improve the surface coverage, the braiding can be encased in a film, such as Teflon, silicone, or another plastic which the body can tolerate. To increase the flexibility and stretchability, such a plastic film can be slit, the arrangement of the slits being staggered and the longitudinal direction of the slits running along the contour of the implant. Such a film can be achieved for example by dipping the implant into a corresponding liquid film material (dispersion or solution) and then making the slits, for example with a laser. By dipping, it is also possible to accomplish, for example, a partial or complete filling out of the meshes.

Alternatively, it is possible to encase the individual filaments of the implant with such a plastic by dipping into a plastic dispersion or solution and thereby increase the filament cross section. In this case, open meshes remain, but the mesh size is diminished significantly.

The implant may also be coated in a manner known per se. The coating materials may be in particular those which are described for stents, such as materials with antiproliferative, antiinflammatory, antithrombogenic, growth-promoting and/or deposit-preventing hemocompatible properties. Preferable is a coating which encourages the ingrowth of the implant and the formation of neointima. It may be advisable to coat the implant in this way on the outside, and on the inside with an agent which lessens adhesion, such as heparin or a derivative, ASS, or suitable oligosaccharides and chitin derivates. Also suitable for this are layers of nano-particles, such as ultrathin layers of polymeric SiO2, which lessen adhesion.

As already mentioned above, in the first embodiment of the invention the combination of insertion wire with holding element, release tube and implant is led through a microcatheter. The diameter of the holding element and the release tube in this case is dimensioned so that the two together can easily be led through a conventional microcatheter. Accordingly, the invention also concerns a device which comprises, besides the implant, the release tube and the insertion wire, also a microcatheter through which the other components can be brought to the target location. Furthermore, the device may comprise a storage sleeve in which the implant and optionally the release tube and insertion wire can be kept for storage. For use, the implant is pulled out from the storage sleeve with the aid of the insertion wire and shoved into the microcatheter, typically making use of a conical transition piece.

BRIEF DESCRIPTION OF THE DRAWINGS

The invention shall now be explained more closely as an example with the aid of the following representations. There are shown:

FIG. 1a, b: a device with distal insertion wire tip according to a first embodiment of the invention;

FIG. 2a, b: a device without distal insertion wire tip according to the first embodiment of the invention, FIG. 3a, b: the holding element in transverse and longitudinal cross section according to the first embodiment of the invention;

FIG. 4: a holding element in longitudinal cross section with secured implant according to the first embodiment of the invention;

FIG. 5: a device according to the invention in longitudinal cross section according to a second embodiment of the invention;

FIGS. 6-11: different variants of a release tube according to the second embodiment of the invention.

DESCRIPTION OF THE INVENTIONS

Figure 8:
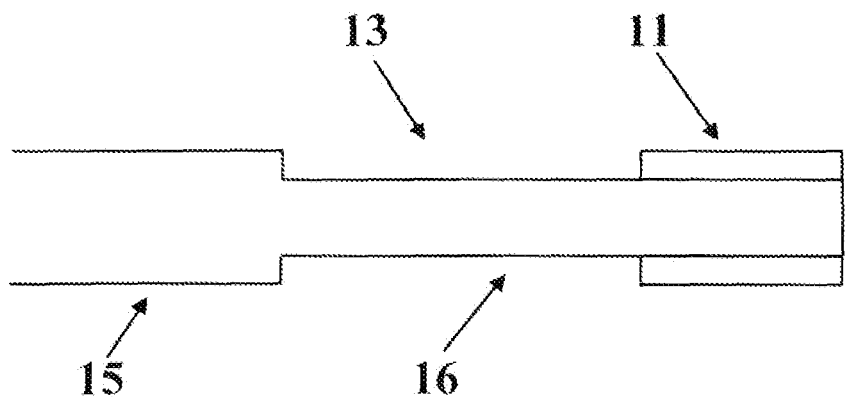

FIG. 1a shows the basic layout of the device of the invention according to the first embodiment of the invention, where the specific properties of the holding element cannot be seen in this representation. The device is composed of an implant 1, an insertion wire 14 and a release tube 13. The implant 1 consists of a braiding, in which individual wires 4 of a radiopaque material are interwoven in order to ensure the radiopacity of the implant 1. At the proximal end, the implant 1 is coupled to the insertion wire 14, which has a holding element not represented here in further detail. The holding wires emerging from the proximal end of the implant 1 are fixed in the holding element, wherein the release tube 13 prevents the holding wires from being loosened from the holding element. The insertion wire 14 runs in the distal direction through the implant 1 and has at the distal end an insertion wire tip 9. The implant 1 is advanced through a microcatheter 8. At the proximal end, the insertion wire 14 and the release tube 13 are held together by a torquer 7.

FIG. 1b shows the implant 1 of FIG. 1a in the released state. The release tube 13 has been retracted, so that the holding wires could become loosened from the holding element of the insertion wire 14. The insertion wire tip 9 still runs through the implant 1, but it can be retracted together with the insertion wire 14 and release tube 13.

FIGS. 2a and 2b show an embodiment which corresponds fundamentally to the one from FIGS. 1a and 1b, but here there is no distal insertion wire tip 9.

FIG. 3a shows the holding element 2 in cross section. The holding element 2 is basically substantially cylindrical and thus rotationally symmetrical. A number of grooves 3 have been recessed in the holding element 2, the number of grooves 3 being four in the example chosen here. However, it is also possible to make more grooves 3 in the holding element, such as 8-32 grooves 3. The grooves 3 are open on the outside, so that it is possible to insert a holding wire 5.

The course of the grooves 3 is shown in FIG. 3b, which is a longitudinal cross section through the holding element 2. The holding element 2 is fastened to the insertion wire 14. The grooves 3 have a wave-shaped course, and so the holding wires 5 can be inserted such that a sufficiently strong frictional locking is produced, preventing the implant 1 from being pulled out in the longitudinal direction. On the other hand, the grooves 3 are open radially outward, so that a radial exiting of the holding wires 5 is easily possible as soon as a release tube 13 pulled over the holding element 2 and the holding wires 5 has been removed. The grooves 3 of the holding element 2 located at the edge are only suggested in FIG. 3b, but they have the same wave-shaped course as the other grooves 3.

The overall principle of the releasing is further illustrated in FIG. 4, showing the proximal implant end 12. In the representation chosen here and in FIG. 3b, contrary to the representations chosen in FIGS. 1a,b and 2a,b, left corresponds to distal, while the device continues to the right in the proximal direction. The implant 1 is composed of a plurality of braiding wires 6. Of the braiding wires 6, some braiding wires 6 have a lengthened proximal end, the lengthening producing the holding wire 5 which is inserted into a groove 3. The number of holding wires 5 normally corresponds to the number of grooves 3. Thanks to a wave-shaped course of the groove 3, a corresponding wave shape is also imposed on the holding wire 5, so that the holding wire 5 is held in the groove 3 by means of frictional locking. The stiffness of the holding wire 5 should be attuned to the device so that an unintentional pulling of the holding wire 5 out from the groove 3 is virtually impossible for the pushing or pulling forces typically occurring in the implantation process. Typically, every 2nd, 4th, or 8th braiding wire 6 is formed longer, so that a holding wire 5 is produced. Furthermore, some of the braiding wires 6 have a platinum coil 10, which serves to heighten the radiopacity of the implant 1.

The release tube 13 is pulled over both the holding element 2 and the proximal implant end 12. This ensures on the one hand that a releasing of the implant 1 cannot occur before the release tube 13 has been pulled down from the holding element 2 enough so that all of the grooves 3 are exposed. On the other hand, the fact that the release tube 13 is also pulled over the proximal implant end 12 ensures that even after releasing of the implant from the microcatheter the braiding wires 6 are held together at the proximal end 12 and a retraction into the microcatheter 8 still remains possible if needed, as long as the release tube 13 has not been retracted.

FIGS. 5-11 show the second embodiment of the invention. The release tube 13 comprises at its distal end one or more pads 11, which are made from an elastic material and create a sufficiently strong frictional locking between pad 11 and implant 1 so that an advancement and retraction of the implant 1 is possible by moving the release tube 13. The implant 1 in the representation chosen here is located inside the microcatheter 8, i.e., in its compressed form. The insertion wire 14 extends here through the entire implant, so that the insertion wire tip 9 lies distally to the distal end of the implant, but an insertion wire tip 9 is not obligatory. In contrast to the representation which was chosen in FIGS. 3a, 3b and 4, in the representation of FIGS. 5-11 proximal lies to the left and distal to the right. At the proximal end of the device, the insertion wire 14 and the release tube 13 are held by means of a torquer 7.

Once the implant 1 has arrived at the target location, it can be pushed distally out from the microcatheter 8 or the microcatheter 8 can be retracted proximally, so that the implant 1 expands radially and adapts to the inner wall of the vessel. As in the first embodiment of the invention, the release principle is thus based on the fact that a releasing occurs by an expansion of the implant 1 in the radial direction, while sufficiently large frictional forces are generated in the axial direction to prevent a releasing of the implant 1 in the axial direction.

FIGS. 6-11 show different variants of release tubes 13. In the embodiment represented in FIG. 6, a proximal section 15 of the release tube 13 has a larger cross section, while a further distally situated middle section 16 has a smaller cross section. This means that on the one hand the middle section 16 of the release tube 13 is quite flexible and can be advanced easily during the transport through narrow-lumen blood vessels, while on the other hand the release tube 13 can also be retracted easily in the proximal direction, since the proximal section 15 has a larger cross section and thus limits the lengthwise stretchability of the release tube 13. According to FIG. 6, the pad 11 is made from the tube material itself, i.e., no pad 11 needs to be arranged additionally on the release tube 13.

FIG. 7 shows a similar embodiment, in which the middle section 16 likewise has a smaller cross section than the proximal section 15 of the release tube 13. In contrast to the representation shown in FIG. 6, however, two pads 11 are arranged here separately, surrounding the release tube 13 like a ring.

FIG. 8 shows a further variant, in which the proximal section 15 likewise has a larger cross section than the further distally situated middle section 16 of the release tube 13, but here only one pad 11 has been arranged surrounding the release tube 13 in a ring, being longer in configuration than the individual pads of FIG. 7.

Figure 9:
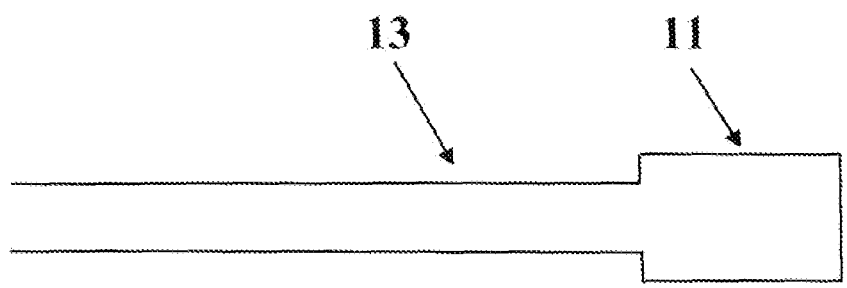
Figure 10:
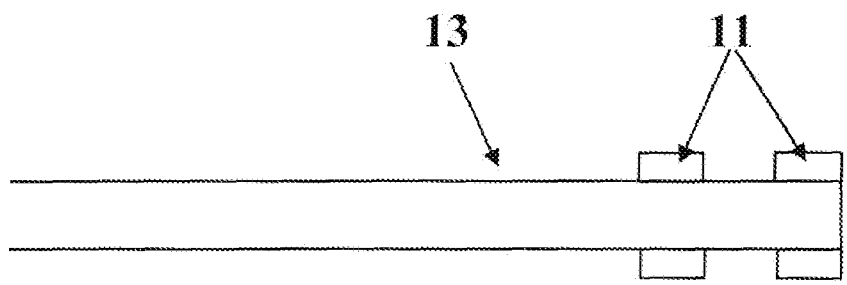
Figure 11:
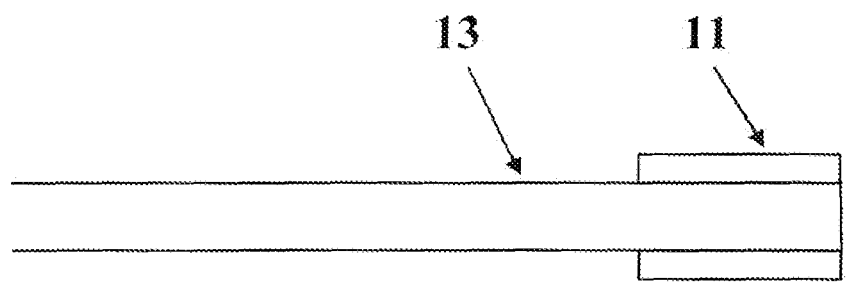

FIGS. 9, 10 and 11 correspond to FIGS. 6, 7 and 8, but the release tube 13 has no shoulder and, seen from the distal end, has a uniform cross section.

Figure 12:
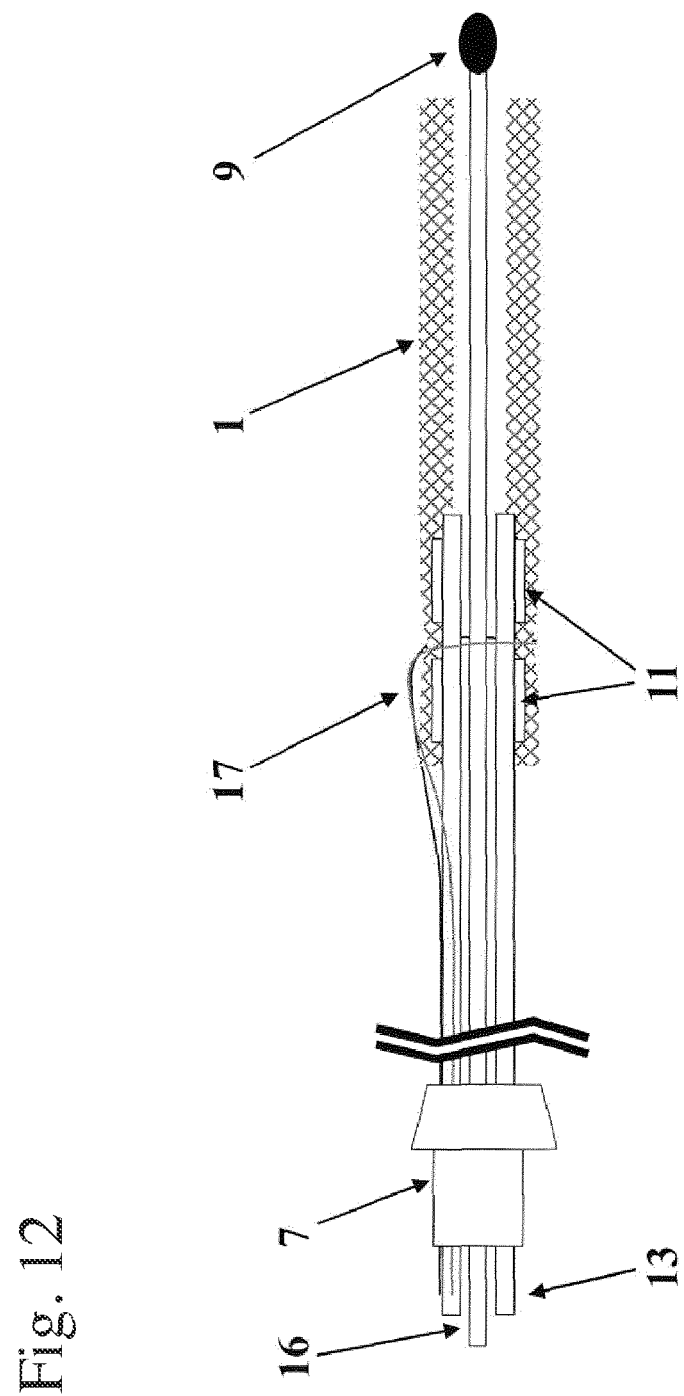
FIG. 12: a variant of the second embodiment of the invention in which a release wire is used.

FIG. 12 shows a variant in which a frictional locking is produced between the implant 1 and the release tube 13 by winding a release wire 17 about the implant 1. The release wire 17 ties the implant 1 between two pads 11 such that a fixation of the implant 1 on the release tube 13 is produced. Thus, even without a microcatheter, the implant 1 remains secured on the release tube 13 until an electrical voltage is applied and produces an electrolytic corrosion of the release wire 17 at a designated release site and the release wire is detached from the implant 1. After this, the implant 1 can expand and the microcatheter, the release tube 13, the insertion wire 14 as well as the remaining ends of the release wire 17 are retracted. To enable an electrical voltage source to be applied to the release wire 17, the two ends of the release wire 17 run in the proximal direction.

We claim:

1. A device for introducing an implant (1) into blood vessels or hollow organs of the human or animal body, comprising:
   an implant (1),
   an insertion wire (14) and
   a release tube (13), wherein
   the implant (1) is deformable so that it adopts a shape with reduced diameter when constrained in a microcatheter (8) and at the site of the implantation it expands once unconstrained by the microcatheter (8), adapting to the diameter of the blood vessel or hollow organ, wherein a holding element (2) is arranged on the insertion wire (14), characterized in that the holding element (2) has at its periphery at least one groove (3) set into the holding element (2), running along the circumference of the holding element (2) and forming at least one track in the form of a curved line , wherein
   the implant (1) has at a proximal end at least one holding wire (5) extending in a proximal direction, with each holding wire fitted into a corresponding groove (3), wherein the release tube (13) is pulled with a form fit over the holding element (2) and each holding wire is (5) fitted into a corresponding groove (3), so that each holding wire is held in a corresponding groove (3) by frictional locking and release of the implant (1) occurs by pulling back the release tube (13) in the proximal direction.

2. The device as claimed in claim 1, characterized in that each groove (3) on the circumference of the holding element (2) forms a wave-shaped track.

3. The device as claimed in claim 2, characterized in that each groove (3) on the circumference of the holding element (2) runs from the proximal direction to a distal direction.

4. The device as claimed in claim 1, characterized in that each groove (3) on the circumference of the holding element (2) runs from the proximal direction to a distal direction.

5. The device as claimed in claim 1 , characterized in that the number of grooves (3) in the holding element (2) is ≥4.

6. The device as claimed in claim 5, characterized in that the number of grooves (3) in the holding element (2) is ≥8.

7. The device as claimed in claim 6, characterized in that the number of grooves (3) in the holding element (2) is 8 to 32.

8. The device as claimed in claim 1, characterized in that the cross section of each groove (3) is slightly larger than the cross section of the holding wires (5).

9. The device as claimed in claim 1, characterized in that the implant (1) is a braiding made from a plurality of braiding wires (6).

10. The device as claimed in claim 9, characterized in that the holding wires (5) are proximal sections of the braiding wires.

11. The device as claimed in claim 10, characterized in that some of the braiding wires (6) are lengthened in the proximal direction.

12. The device as claimed in claim 1, characterized in that the release tube (13), prior to the retraction in the proximal direction, covers the proximal end of the implant (1).

13. The device as claimed in claim 1, characterized in that the holding wires (5) are deformed in a manner increasing the frictional forces between the holding wires (5) and the grooves (3).

14. The device as claimed in claim 1, characterized in that each groove (3) on the circumference of the holding element (2) forms a sinusoidally wave-shaped track.

15. The device of claim 14, wherein each holding wire fitted into a corresponding groove (3) has a sinusoidal shape corresponding to the sinusoidally wave-shaped track.

16. The device of 1, wherein:
 the implant is a tubular implant having a lumen passing through the tubular implant;
 the holding wires do not extend radially into the lumen.

* * * * *